United States Patent [19]

Bhattacharya

[11] Patent Number: 4,761,467

[45] Date of Patent: Aug. 2, 1988

[54] PYRIDINE LIGANDS FOR PREPARATION OF ORGANIC CARBONATES

[75] Inventor: Ajit K. Bhattacharya, Hopewell Junction, N.Y.

[73] Assignee: Texaco Inc., White Plains, N.Y.

[21] Appl. No.: 789,809

[22] Filed: Oct. 21, 1985

[51] Int. Cl.[4] ............................................. C07C 68/00
[52] U.S. Cl. .................................... 558/277; 502/165; 502/171; 556/113; 558/260; 558/270; 558/274
[58] Field of Search ............... 558/277, 260, 270, 274; 502/165, 171; 556/113

[56] References Cited

U.S. PATENT DOCUMENTS

| | | | |
|---|---|---|---|
| 3,846,468 | 11/1974 | Perrotti et al. | 558/277 |
| 4,218,391 | 8/1980 | Romano et al. | 558/277 |
| 4,318,862 | 3/1982 | Romano et al. | 558/277 |
| 4,625,044 | 11/1986 | Curnutt | 558/277 |

Primary Examiner—Werren B. Lone
Assistant Examiner—Vera C. Clarke
Attorney, Agent, or Firm—Robert A. Kulason; James J. O'Loughlin; Vincent A. Mallare

[57] ABSTRACT

An organic carbonate such as dimethyl carbonate is prepared by reacting an alcohol such as methanol with carbon monoxide and oxygen in the presence of a catalyst system containing Cu(OMe)Cl as a catalyst and a pyridine compound as a ligand of the catalyst system.

9 Claims, No Drawings

PYRIDINE LIGANDS FOR PREPARATION OF ORGANIC CARBONATES

BACKGROUND OF THE INVENTION

1. Field of the Invention

This invention relates to the preparation of organic carbonates. More particularly it relates to ligands for the preparation of dimethyl carbonate (DMC). DMC may be used as a gasoline extender and octane enhancer, as an organic solvent, or as a reactant in place of phosgene in the preparation of isocyanates, polycarbonates, and various agricultural and pharmaceutical intermediates.

Dimethyl carbonate (DMC) may be prepared by the reaction of methanol with carbon monoxide and oxygen in the presence of a catalyst system. Those skilled in the art, constantly seek new or improved catalysts or ligands for such catalysts to lower costs, to improve reaction conditions, yield and rate of production, and to facilitate separation of reactants, products, and catalysts.

Thus, it is an object of this invention to provide an improved method of preparing dimethyl carbonate, lower the cost of the process, substantially increase the yield and rate of production of dimethyl carbonate, and ease the separation of DMC and water from the catalyst system.

2. Disclosure Statement

U.S. Pat. No. 3,114,762 discloses as catalysts metal salts including chlorides and bromides of platinum and palladium plus an oxidizing agent such as iron or copper salts having the same anion.

U.S. Pat. No. 3,227,740 discloses as catalyst mercuric halides or carboxylates.

Saegusa et al, *J. Org Chem.*, 35, 2976–2978 (1970) discloses the reaction of CO with copper alkoxides including the dimethoxide, the diallyloxide, the chloride methoxide, and the acetylacetonate methoxide.

Romano et al IEC Prod. Res. Dev. 19, 396–403 (1980) discloses as catalyst cuprous chloride/cupric chloride methoxide.

U.S. Pat. No. 4,218,391 discloses as catalysts salts of metals of Group IB, IIB, and VIII, preferably monovalent copper such as cuprous bromide, chloride, or perchlorate.

U.S. Pat. No. 4,318,862 discloses as catalyst salts of metals of Groups IB, IIB, or VIII, typically a copper salt such as CuCl.

U.S. Pat. No. 3,846,468 discloses as catalysts cuprous chloride complexes with various organic compounds such as pyridine, dipyridyl, imidazole, phenanthroline, alkyl, or aryl phosphines, dimethyl sulfoxide, dimethyl formamide, quinuclidine, acetonitrile, benzonitrile, malonitrile, succinodinitrile, or adiponitrile.

U.S. Pat. No. 3,980,690 discloses as catalyst a complex of copper chloride and poly-4-vinylpyridine.

Rivetti et al, *J. Organometallic Chem*, 174 (1979) 221–226 discloses as catalysts palladium (II) complexes in the presence of ligands and added bases. Alkyl phosphines are said to inhibit carbonylation almost completely. The presence of tertiary amines enhances the formation of dimethyl carbonate. Low yields (6% or less) of dimethyl carbonate are obtained with $Pd(OAc)_2$ in the presence of ligands such as $R_3P$ where R is p-$C_6H_4OCH_3$. Yield is increased to 61% in the presence of a base such as diisopropylethylamine.

U.S. Pat. No. 3,952,045 discloses as catalysts organic phosphorus compounds such as phosphine oxide, phosphite, phosphate, or phosphonate plus copper halides.

U.S. Pat. No. 4,360,477 dicloses as catalysts cupric halides inter alia.

Yang et al CA 86, 17186u (1977) discloses as catalysts $PdCl_2$, $CuCl_2$, $MnCl_2$, and LiCl.

Lapidus et al CA 93, 72338j (1980) discloses as catalyst $MnCl_2$, $KMnO_4$, $CuCl_2$, LiCl, and $Mn(OAc)_3$.

Itatani, Japanese patent publication No. 54-24827 pub 24 Feb. 1979 discloses as catalyst a cuprous halide plus as auxiliary catalyst a halide of an alkali metal or an alkaline earth metal.

U.S. Pat. No. 4,370,275 discloses as catalyst compositions containing copper, chemically bonded oxygen, and halogen and a nitrogen base. A typical catalyst contains CuO or $Cu(OCl)_2$ and n-butylamine inter alia. Preferred combinations include: $CuCO_3$, $Cu(OH)_2$; $CuCl_2$ and pyridine hydrochloride etc.

U.S. Pat. No, 4,131,521 discloses an electrochemical process utilizing a non-fluoride halide-containing electrolyte.

U.S. Pat. No. 4,113,762 discloses as catalyst a complex of copper (as CuCl) with $VCl_3$, $CrCl_3$, $FeCl_3$, $CoCl_2$, $AlCl_3$, or $SiCl_4$.

U.S. Pat. No. 4,361,519 discloses as catalyst (i) a Bronsted base such as a quaternary ammonium, phosphonium, or sulfonium compound or an alkoxide or hydroxide of alkali metal or alkaline earth metal or a salt of a strong base and a weak acid or amines etc. plus (ii) a Group VIII B element Ru, Rh, Pd, Os, Ir or Pt plus (iii) oxygen plus (iv) a redox catalyst such as a Mn or Co containing catalyst. A typical system includes (i) a pentamethylpiperidine, (ii) $PdBr_2$ and (iii) pyridine adduct of salicylaldehyde-ethylene diamine Co (II) complex.

European Pat. No. 0,071,286 discloses as catalyst a copper compound such as a halide (in the presence of an amine) plus a sulphone such as dimethyl sulphone or sulfolane.

SUMMARY OF THE INVENTION

This invention is directed to a method of preparing an organic carbonate $R'_2CO_3$ wherein $R'$ is a hydrocarbon group selected from the group consisting of alkyl, alkaryl, aralkyl, cycloalkyl, and aryl hydrocarbon groups. The method comprises reacting an alcohol with carbon monoxide and oxygen in the presence of a catalyst system containing (a) as a catalyst, a copper hydrocarbonoxy halide $Cu(OR'')X$ wherein $R''$ is a hydrocarbon group selected from the group consisting of alkyl, alkaryl, aralkyl, cycloalkyl, and ary and X is a halide; and (b) as a ligand of the catalyst, a pyridine compound of the formula

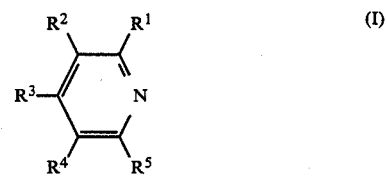

(I)

wherein $R^1$, $R^2$, $R^3$, $R^4$, and $R^5$ may each be H, F, Cl, Br, I, $NO_2$, R, OR, SR, CN, COOR, or $NR^6R^7$ where R is a ($C_1$-$C_{10}$) alkyl, aralkyl, cycloalkyl, aryl or alkaryl group; $R^6$ and $R^7$ are each a ($C_1$-$C_8$) alkyl group, or $R^6$ and $R^7$ combined are ($C_3$-$C_8$) alkylene or oxa-, thia-, or aza-alkylene groups, and where said pyridine ring is mono, di, tri, tetra, or penta substituted; and recovering the organic carbonate product.

DESCRIPTION OF THE INVENTION

In preparing organic carbonates according to the present invention, a pyridine compound is used as a ligand of the catalyst which substantially increases the rate of production of the organic carbonate. An organic carbonate such as dimethyl carbonate is prepared by the oxidative carbonylation of alcohols in the presence of a catalyst and a pyridine ligand of the present invention.

The organic carbonate, e.g., dimethyl carbonate, is prepared by reacting an alcohol with carbon monoxide and oxygen in the presence of a catalyst system containing (a) as a catalyst, a copper hydrocarbonoxy halide Cu(OR")X wherein R" is a hydrocarbon group selected from the group consisting of alkyl, alkaryl, aralkyl, cycloalkyl, and aryl and X is a halide; and (b) as a ligand of the catalyst, a pyridine compound of the formula

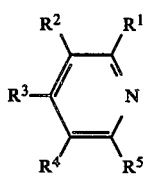

wherein $R^1$, $R^2$, $R^3$, $R^4$, and $R^5$ may each be H, F, CL, Br, I, $NO_2$, R, OR, SR, CN, COOR, or $NR^6R^7$ where R is a ($C_1$–$C_{10}$) alkyl, aralkyl, cycloalkyl, aryl or alkaryl group; $R^6$ and $R^7$ are each a ($C_1$–$C_8$) alkyl group, or $R^6$ and $R^7$ combined are ($C_3$–$C_8$) alkylene or oxa-, thia-, or aza-alkylene groups, and where said pyridine ring is mono, di, tri, tetra, or penta substituted; and recovering the organic carbonate product.

The charge alcohol which may be employed in practice of the method of this invention may include those characterized by the formula R'OH.

In the above compound, R' may be a hydrocarbon group selected from the group consisting of alkyl, aralkyl, cycloalkyl, aryl, and alkaryl, including such radicals when inertly substituted. When R' is alkyl, it may typically be methyl, ethyl, n-propyl, iso-propyl, n-butyl, i-butyl, sec-butyl, amyl, octyl, decyl, octadecyl, etc. When R' is aralkyl, it may typically be benzyl, beta-phenylethyl, etc. When R' is cycloalkyl, it may typically be cyclohexyl, cycloheptyl, cyclooctyl, 2-methylcycloheptyl, 3-butylcyclohexyl, 3-methylcyclohexyl, etc. When R' is aryl, it may typically be phenyl, naphthyl, etc. When R' is alkaryl, it may typically be tolyl, xylyl, etc. R' may be inertly substituted i.e. it may bear a non-reactive substituent such as alkyl, aryl, cycloalkyl, ether, etc. Typically inertly substituted R' groups may include 2-ethoxyethyl, carboethoxymethyl, 4-methyl cyclohexyl, etc. The preferred R' groups may be lower alkyl, i.e. $C_1$–$C_{10}$ alkyl, groups including methyl, ethyl, n-propyl, i-propyl, butyls, amyls, hexyls, octyls, decyls, etc. R' may preferably be methyl.

The charge alcohol may be a phenol i.e. when R' is aryl. The notation R'OH is intended to include polyols such as ethylene glycol, glycerine, sorbitol, poly(oxyalkylene)polyols, etc; in these latter compounds, the formula may more typically be represented as $R'(OH)_n$ wherein R' is derived from an alkyl group and n is an integer, typically 2–10.

The charge alcohols which may be employed include these listed below in Table I.

TABLE I methanol
ethanol
n-propanol
i-propanol
benzyl alcohol
phenol
ethylene glycol
glycerine
sorbitol
poly(oxyethylene-10)glycol The preferred alcohols are the lower ($C_1$–$C_4$) alkanols; and most preferred is methanol.

The carbon monoxide charge which may be employed may be a pure gas. More commonly it may be a synthesis gas of high purity from which most of the hydrogen and carbon dioxide have been removed.

The catalyst, i.e., copper hydrocarbonoxy halide Cu(OR")X may be one wherein X is fluorine, chlorine, bromine, or iodine. Preferably X is chlorine or bromine and more preferably chlorine.

R" may be selected from the same group as R'; and preferably R" is a lower alkyl i.e. $C_1$–$C_{10}$ alkyl. Preferably R" is methyl. Typical compounds may include those listed below in Table II. The preferred catalyst being the first listed, i.e., cupric methoxychloride.

TABLE II

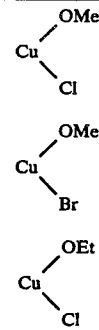

The copper salt catalyst system containing Cu(II)-(OMe)Cl/Cu(I)Cl is only sparingly soluble in methanol and the rate of DMC formation is undesirably low. This invention relates to the large increase in the yield and rate of organic carbonate formation in the presence of a pyridine ligand. Thus, the rate of DMC production is significantly augmented in the presence of 4-dimethylaminopyridine (4-DMAP) as a ligand for the catalyst concerned. According to the present invention, it has been found that the rate of DMC formation in the presence of 4-DMAP is several times higher than that under similar conditions in either triethylamine or dimethylaminobenzene. An additional advantage of 4-DMAP is that 4-DMAP (mp 108°–110° C.) is not volatile and remains with the catalyst during any subsequent separation of the reaction mixture by any flash or distillation method.

The ligand of the catalyst may be a pyridine compound of the formula

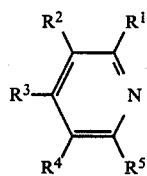
(I)

where $R^1$, $R^2$, $R^3$, $R^4$, and $R^5$ may each be H, F, Cl, Br, I, $NO_2$, R, OR, SR, CN, COOR, or $NR^6R^7$ where R is a ($C_1$–$C_{10}$) alkyl, aralkyl, cycloalkyl, aryl or alkaryl group; $R^6$ and $R^7$ are each a ($C_1$–$C_8$) alkyl group, or $R^6$ and $R^7$ combined are ($C_3$–$C_8$) alkylene or oxa-, thia-, or aza-alkylene groups, and where said pyridine ring is mono, di, tri, tetra, or penta substituted; and recovering the organic carbonate product.

The pyridine compounds, according to the present invention may include 4-dimethylaminopyridine, 2-diethylaminopyridine, methyl isonicotinate, N,N-dimethylnicotinamide, 4-methoxypyridine, 2-(methylthio)pyridine, 4-tertiary-butylpyridine, pyridine, 4-(morpholino)pyridine, 4-(N-methylpiperazino)pyridine, 2,2'-dipyridyl, or 2-pyridyl-2'-pyrimidyl.

Also, according to formula (I), the pyridine compounds may be represented by the following formulas:
4-dimethylaminopyridine [where $R^3$ is $N(CH_3)_2$]

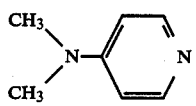

2-diethylaminopyridine [where $R^1$ is $N(C_2H_5)_2$]

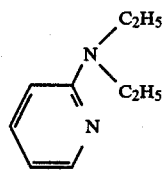

methyl isonicotinate [where $R^3$ is $(COOCH_3)$]

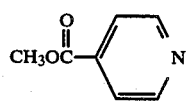

N,N-dimethylnicotinamide [where $R^2$ is $CON(CH_3)_2$]

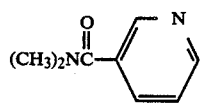

4-methoxypyridine [where $R^3$ is $(CH_3O)$]

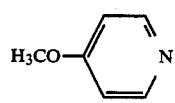

2-(methylthio)pyridine [where $R^1$ is $(SCH_3)$]

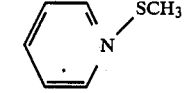

4-tertiary-butylpyridine [where $R^3$ is $C(CH_3)_3$]

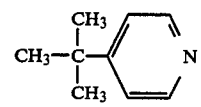

pyridine (where $R^3$ is H)

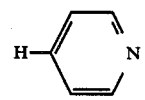

4-(morpholino)pyridine [where $R^3$ is 4-(morpholino)]

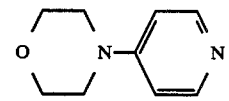

4-(n-methylpiperazino)pyridine [where $R^3$ is 4-(N-methylpiperazino)]

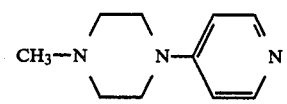

2,2'-dipyridyl [where $R^1$ is 2'-pyridino]

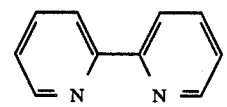

2-pyridyl-2'-pyrimidyl [where $R^1$ is 2'-pyrimidyl]

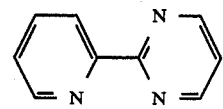

2,3-dimethylpyridine [where $R^1$ and $R^2$ are each $CH_3$]

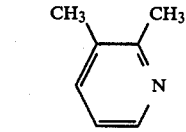

pentachloropyridine [where $R^1$, $R^2$, $R^3$, $R^4$, and $R^5$ are each Cl]

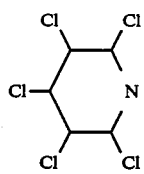

In another embodiment of the present invention, there are other pyridine and pyrimidine derived compounds, which may be used as a ligand of the catalyst. These include the heterocyclic compounds provided below in Table III.

TABLE III 2,2'-dipyrimidyl

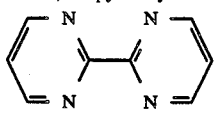

1,10-Phenanthroline

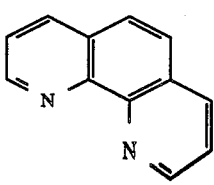

Quinoline

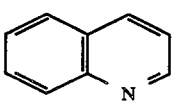

Isoquinoline

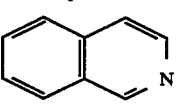

The catalyst system may be present in the reaction mixture in an amount of about 0.1 to about 50 parts, preferably about 0.1 to about 20 parts, and more preferably about 10 parts per 100 parts of charge methanol. The pyridine compounds may be present in an amount of 0.1 to 10.0 moles, preferably 0.5–4.0 moles, and more preferably 1.0 mole per mole of catalyst.

The practice of the method of this invention may be carried out by adding 100 parts of an optimum mixture of the alcohol R'OH, such as methanol and a pyridine compound to the reaction mixture. The catalyst system may then be added. The system is then subjected to inert gas typically nitrogen at a partial pressure of 5–1000 psi, preferably 100–300 psi, say about 100 psi and heated to 20° C.–170° C., preferably 80°–120° C., say about 90° C. at a total pressure of 10–2000 psi, preferably 150–600 psi, say about 150 psi over 0.25–2 hours, say about 0.5 hour.

Carbon monoxide-containing gas is then admitted to a carbon monoxide partial pressure of 5–300 psi, preferably 100–900 psi, say 350 psi over 0.25–10 hours, say 1 hour.

During this period, the following reaction occurs in the preferred embodiment:

2Cu(OMe)Cl+CO→(MeO)$_2$CO+2CuCl.

At the end of this time, the reaction mixture may be rapidly cooled to 20° C.–90° C., say 25° C. at a total pressure of 15–3000 psi, say 350 psi.

The reaction mixture may be depressured and then distilled to azeotropically distill off various fractions containing methanol, dimethyl carbonate and water. The product may be further treated to effect greater purification of the impure dimethyl carbonate.

The residual catalyst system (0.1–50 parts, say 10 parts) may be regenerated by contacting with an oxygen-containing gas, typically air at 20° C.–65° C., say 45° C. for 1–50 hours, say 6 hours in the presence of excess alcohol, typically methanol in an amount of 100 parts.

During this regeneration step, the following reaction occurs in the preferred embodiment:

2CuCl+2MeOH+½O$_2$→2Cu(OMe)Cl+H$_2$O

At the end of the regeneration period, the catalyst in methanol may be recycled if the water content is less than about 1.0 wt%. If more water than this is present, the catalyst may be separated and then dried by heating to 30° C.–60° C., preferably to 40° C. (under reduced pressure) for 1–10 hours, preferably for 6 hours to yield a substantially anhydrous catalyst system which is recycled using anhydrous methanol.

Practice of the method of this invention will be apparent to those skilled in the art from the following examples, wherein as elsewhere in this specification, all parts are parts by weight unless otherwise noted.

EXAMPLES I–XIII

In these examples which represent the best mode known of practicing the method of this invention, there was added to the reaction vessel 190 ml of anhydrous methanol and 18.2 g (0.14 mol) of anhydrous Cu(OMe)Cl and 0.07 mole of an organic nitrogen base compound including the pyridine ligands of this invention (i.e., triethylamine, pyridine, 4-dimethylaminopyridine, methyl isonicotinate, hexamethylmelamine, 4-tert-butylpyridine, 4,4'-dipyridyl and 2,2'-dipyridyl). In Exapmles I and II, no such ligand was present, and in Example VI, 0.14 mole of pyridine was employed.

In each of the examples, the procedure and conditions were the same except that the nitrogen base compound was different.

The reaction mixture was pressurized to 100 psig with nitrogen, heated to 90° C. and maintained at 90° C. for 0.5 hour. The pressure was increased to 500 psig with carbon monoxide and the stirring was continued. The reaction mixture was then cooled to room temperature, and depressurized. The reaction mixture was distilled with added methanol (200 ml) to recover azeotrope containing methanol and dimethyl carbonate. Analysis by Gas Chromatography indicated the yields (based on copper salt) shown below in Table IV.

Methanol (100 ml) was added and the catalyst was regenerated by bubbling air through the suspension at 45° C. for 6 hours. The regenerated catalyst in this reaction mixture was recycled for reaction with CO under standard reaction conditions as described above. The product was recovered and analyzed for DMC as mentioned above. The numbers in parentheses represent the yield attained in a subsequent run in which the catalyst used has been regenerated, the reaction conditions being otherwise the same.

TABLE IV

| | Production of DMC | | |
|---|---|---|---|
| Example | Nitrogen Base (B) | B/[Cu][1] Mol Ratio | % Yield of DMC[2,3,4] |
| I | None | 0.0 | 8(14) |
| II | None | 0.0 | 19(22)[5] |
| III | Dimethylaminobenzene | 0.5 | 4 |
| IV | Triethylamine | 0.5 | 3(4) |
| V | Pyridine | 0.5 | 51(70) |
| VI | Pyridine | 1.0 | 90[5] |
| VII | 4-Dimethylaminopyridine | 0.5 | 76 |
| VIII | 4-Dimethylaminopyridine | 0.5 | 97[5] |
| IX | Methyl isonicotinate | 0.5 | 42(66)[5] |
| X | Hexamethylmelamine | 0.5 | 19[5] |
| XI | 4-tert-Butylpyridine | 0.5 | 46 |
| XII | 4,4'-Dipyridyl | 0.5 | 2 |
| XIII | 2,2'-Dipyridyl | 0.5 | 74 |

[1][Cu] = Cupric methoxychloride (18.2 g, 0.14 mol)/190 ml methanol
[2]Reaction conditions: 90° C./500 psig N$_2$:CO (3:7)/15 min.
[3]Gas chromatographic analyses were employed to determine the yield based on copper salt added and 100% DMC product selectivity.
[4]The numbers in parentheses represent the yield attained in a subsequent run in which the catalyst used has been regenerated, the reaction conditions being otherwise the same.
[5]Reaction conditions were the same as in footnote 2 excepting that the reaction time was 30 minutes.

As shown in Table IV above, the addition of a pyridine ligand of the present invention greatly increased the yield of dimethyl carbonate (DMC). In fact, the yield was more than 3 to 9 times the yield when methanol was used alone. It is apparent that the process of this invention makes it possible to obtain higher yields of DMC in shorter time, i.e., to increase the rate of formation of desired dimethyl carbonate.

Although this invention has been illustrated by reference to specific embodiments, it will be apparent to those skilled in the art that various changes and modifications may be made which already fall within the scope of this invention.

I claim:

1. A method of preparing dimethyl carbonate which comprises
    (a) reacting methanol with carbon monoxide and oxygen in the presence of a catalyst system containing
        (i) as a catalyst, cupric methoxychloride [Cu(O-Me)Cl], and
        (ii) as a ligand of the catalyst, a pyrimidine compound; and
    (b) recovering the dimethyl carbonate product.

2. The method of claim 1, wherein the pyrimidine compound is 2,2'-dipyrimidyl

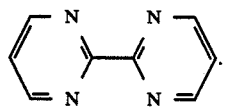

3. A method of preparing dimethyl carbonate which comprises
    (a) reacting methanol with carbon monoxide and oxygen in the presence of a catalyst system containing
        (i) as a catalyst, cupric methoxychloride [Cu(O-Me)Cl], and
        (ii) as a ligand of the catalyst, methyl isonicotinate; and
    (b) recovering the dimethyl carbonate product.

4. A method of preparing dimethyl carbonate which comprises
    (a) reacting methanol with carbon monoxide and oxygen in the presence of a catalyst system containing
        (i) as a catalyst, cupric methoxychloride [Cu(O-Me)Cl], and
        (ii) as a ligand of the catalyst, 4-methoxypyridine; and
    (b) recovering the dimethyl carbonate product.

5. A method of preparing dimethyl carbonate which comprises
    (a) reacting methanol with carbon monoxide and oxygen in the presence of a catalyst system containing
        (i) as a catalyst, cupric methoxychloride [Cu(O-Me)Cl], and
        (ii) as a ligand of the catalyst, 2-(methylthio)pyridine; and
    (b) recovering the dimethyl carbonate product.

6. A method of preparing dimethyl carbonate which comprises
    (a) reacting methanol with carbon monoxide and oxygen in the presence of a catalyst system containing
        (i) as a catalyst, cupric methoxychloride [CU(O-Me)Cl], and
        (ii) as a ligand of the catalyst, 4-(morpholino)pyridine; and
    (b) recovering the dimethyl carbonate product.

7. A method of preparing dimethyl carbonate which comprises
    (a) reacting methanol with carbon monoxide and oxygen in the presence of a catalyst system containing
        (i) as a catalyst, cupric methoxychloride [CU(O-Me)Cl], and
        (ii) as a ligand of the catalyst, 4-(N-methylpiperazine)pyridine; and
    (b) recovering the dimethyl carbonate product.

8. A method of preparing dimethyl carbonate which comprises
    (a) reacting methanol with carbon monoxide and oxygen in the presence of a catalyst system containing
        (i) as a catalyst, cupric methoxychloride [CU(O-Me)Cl], and
        (ii) as a ligand of the catalyst, 2-pyridyl-2'-pyrimidiyl; and
    (b) recovering the dimethyl carbonate product.

9. A method of preparing dimethyl carbonate which comprises
    (a) reacting methanol with carbon monoxide and oxygen in the presence of a catalyst system containing
        (i) as a catalyst, cupric methoxychloride [CU(O-Me)Cl], and
        (ii) as a ligand of the catalyst, pentachloro-pyridine; and
    (b) recovering the dimethyl carbonate product.

* * * * *